US012702671B2

(12) United States Patent
Dyhrfjeld-Johnsen

(10) Patent No.: US 12,702,671 B2
(45) **Date of Patent: *Aug. 11, 2026**

(54) CALCINEURIN INHIBITORS OF THE SETRON FAMILY FOR THE TREATMENT OF HEARING LOSS

(71) Applicant: SENSORION, Montpellier (FR)

(72) Inventor: Jonas Dyhrfjeld-Johnsen, Lunel-Viel (FR)

(73) Assignee: SENSORION, Montpellier (FR)

( * ) Notice: Subject to any disclaimer, the term of this patent is extended or adjusted under 35 U.S.C. 154(b) by 9 days.

This patent is subject to a terminal disclaimer.

(21) Appl. No.: 17/820,010

(22) Filed: Aug. 16, 2022

(65) Prior Publication Data

US 2022/0387438 A1 Dec. 8, 2022

Related U.S. Application Data

(63) Continuation of application No. 15/574,547, filed as application No. PCT/EP2016/061119 on May 18, 2016, now Pat. No. 11,433,077.

(60) Provisional application No. 62/163,177, filed on May 18, 2015.

(30) Foreign Application Priority Data

May 18, 2015 (EP) .................................... 15167992

(51) Int. Cl.
*A61K 31/538* (2006.01)
*A61K 31/4178* (2006.01)
*A61K 31/4184* (2006.01)
*A61K 31/46* (2006.01)
*A61P 27/16* (2006.01)

(52) U.S. Cl.
CPC ........ *A61K 31/538* (2013.01); *A61K 31/4178* (2013.01); *A61K 31/4184* (2013.01); *A61K 31/46* (2013.01); *A61P 27/16* (2018.01)

(58) Field of Classification Search
CPC .............. A61K 31/538; A61K 31/4178; A61K 31/4184; A61P 27/16
See application file for complete search history.

(56) References Cited

U.S. PATENT DOCUMENTS

| | | | | |
|---|---|---|---|---|
| 4,892,872 | A * | 1/1990 | Tahara | C07D 413/12 514/230.5 |
| 11,433,077 | B2 * | 9/2022 | Dyhrfjeld-Johnsen | A61K 31/46 |
| 11,612,605 | B2 * | 3/2023 | Dyhrfjeld-Johnsen | A61K 31/538 514/230.5 |
| 2003/0229333 | A1 * | 12/2003 | Ashton | A61K 9/0046 514/8.5 |
| 2015/0174148 | A1 | 6/2015 | Brown et al. | |

FOREIGN PATENT DOCUMENTS

| | | | | |
|---|---|---|---|---|
| JP | 2011-528036 | A | 11/2011 | |
| JP | 2015524408 | A | 8/2015 | |
| WO | WO-2005000216 | A2 * | 1/2005 | A61K 31/13 |
| WO | WO-2009033650 | A1 * | 3/2009 | A61K 31/13 |
| WO | 2010/008995 | A2 | 1/2010 | |
| WO | WO-2010133633 | A1 * | 11/2010 | C23C 14/06 |
| WO | WO-2010133663 | A1 * | 11/2010 | A61P 43/00 |
| WO | 2013124416 | A1 | 8/2013 | |

OTHER PUBLICATIONS

Bas et al., "An experimental comparative study of dexamethasone, melatonin and tacrolimus in noise-induced hearing loss". Acta Otolaryngol. Apr. 2009;129(4):385-9.
Crane et al., "Steroids for treatment of sudden sensorineural hearing loss: a meta-analysis of randomized controlled trials". Laryngoscope. Jan. 2015;125(1):209-17.
Di Leo et al., "Late recovery with cyclosporine-A of an autoimmune sudden sensorineural hearing loss". Acta Otorhinolaryngol Ital. Dec. 2011;31(6):399-401.
Dyhrfjeld-Johnsen et al., "Ondansetron reduces lasting vestibular deficits in a model of severe peripheral excitotoxic injury". J Vestib Res. 2013;23(3):177-86.
Filipo et al., "Oral versus short-term intratympanic prednisolone therapy for idiopathic sudden hearing loss". Audiol Neurootol. 2014;19(4):225-33.
Kramer et al., "Calcineurin controls the expression of numerous genes in cerebellar granule cells". Mol Cell Neurosci. Jun. 2003;23(2):325-30.
Lin et al., "Hearing loss and cognitive decline in older adults". JAMA Intern Med. Feb. 25, 2013;173(4):293-9.
McClelland et al., "Role of ciclosporin in steroid-responsive sudden sensorineural hearing loss". Acta Otolaryngol. Dec. 2005;125(12):1356-60.
Naesens & Sarwal, "Monitoring calcineurin inhibitor therapy: localizing the moving target". Transplantation. Jun. 15, 2010;89(11):1308-9.
Naesens et al., "Calcineurin inhibitor nephrotoxicity". Clin J Am Soc Nephrol. Feb. 2009;4(2):481-508.
Shupak et al., "Otoacoustic emissions in the prediction of sudden sensorineural hearing loss outcome". Otol Neurotol. Dec. 2014;35(10):1691-7.
Uemaetomari et al., "Protective effect of calcineurin inhibitors on acoustic injury of the cochlea". Hear Res. Nov. 2005;209(1-2):86-90.
Vallano et al., "Depolarization and Ca(2+) down regulate CB1 receptors and CB1-mediated signaling in cerebellar granule neurons". Neuropharmacology. May 2006;50(6):651-60.
Venail et al., "A protective effect of 5-HT3 antagonist against vestibular deficit? Metoclopramide versus ondansetron at the early stage of vestibular neuritis: a pilot study". Eur Ann Otorhinolaryngol Head Neck Dis. Apr. 2012;129(2):65-8.

(Continued)

*Primary Examiner* — George W Kosturko
(74) *Attorney, Agent, or Firm* — NIXON & VANDERHYE

(57) ABSTRACT

Disclosed is an inhibitor of calcineurin of the setron family for use for treating hearing loss in a subject in need thereof.

17 Claims, 6 Drawing Sheets

(56) References Cited

OTHER PUBLICATIONS

Viberg & Canlon, "The guide to plotting a cochleogram". Hear Res. Nov. 2004;197(1-2):1-10.
Yamashita et al., "Delayed production of free radicals following noise exposure". Brain Res. Sep. 3, 2004;1019(1-2):201-9.
Yang et al., "Quantitative analysis of apoptotic and necrotic outer hair cells after exposure to different levels of continuous noise". Hear Res. Oct. 2004;196(1-2):69-76.
European Search Report, dated Sep. 23, 2015, from corresponding EP 15 167 992.5 application.
International Search Report, dated Jun. 21, 2016, from corresponding PCT/EP2016/061119 application.
Jackson, L. and Silverstein, H., "Meniere's Disease: Diagnosis, Natural History, and Current Management," Aug. 19, 2002, https://www.audiologyonline.com/articles/meniere-s-disease-diagnosis-natural-1161, accessed Jan. 29, 2019.
Shulman, A. and Goldstein, B., "Brain and inner-ear fluid homeostasis, cochleovestibular-type tinnitus, and secondary endolymphatic hydrops," Int. Tinnitus J, 2006;12(1):75-81, abstract only.
Reagan-Shaw, S. et al., "Dose translation from animal to human studies revisited," The FASEB Journal, vol. 22, Mar. 2007, pp. 659-661.
Tsukuda, M. et al., "A randomized crossover comparison of azasetron and granisetron in the prophylaxis of emesis induced by chemotherapy including cisplatin," Kagaku Ryoho, 1995, vol. 22, pp. 1959-1967, abstract only.

* cited by examiner

CALCINEURIN INHIBITORS OF THE SETRON FAMILY FOR THE TREATMENT OF HEARING LOSS

CROSS-REFERENCE TO RELATED APPLICATIONS

This application is a continuation of U.S. Ser. No. 15/574,574 filed Nov. 16, 2017, which was a national stage application, filed under 35 U.S.C. § 371, of International Patent Application No. PCT/EP2016/061119 filed May 18, 2016, which claims the benefit of U.S. Provisional Application No. 62/163,177 filed May 18, 2015, and claims priority to EP 15167992.5 filed May 18, 2015. Each of the previously noted applications is hereby incorporated by reference in their entirety.

FIELD OF INVENTION

The present invention relates to the treatment of hearing loss, in particular calcineurin inhibitors of the setron family for the treatment of sensorineural hearing loss.

BACKGROUND OF INVENTION

Approximately 360 million people worldwide suffer from disabling hearing loss. The percentage of adults with disabling hearing loss increases from about 2% of the population from 45 to 54 years old, to 8.5% ages 55 to 64, and about 25% of those aged 65 to 74 and 50% in subjects of more than 75 years old. Therefore, there is an important need of methods for treating or preventing hearing loss.

Sensorineural hearing loss is caused by damage to the sensory hair cells and neurons of the cochlea and is the most common type of permanent hearing loss. Among adults, the 2 main causes of sensorineural hearing loss are excessive noise exposure and aging, while other causes include but are not limited to illnesses (including but not limited to high blood pressure and diabetes), ototoxic drugs, head trauma, tumors, blast exposure, autoimmune inner ear disease, idiopathic causes, viral and bacterial infections.

Patients suffering from hearing loss have difficulties communicating and frequently develop tinnitus, resulting in reduced quality of life due to feelings of loneliness, isolation, frustration, anxiety and depression. Hearing loss furthermore has a severe impact on language development in children, education and employment opportunities. A further complication of sensorineural hearing loss include accelerated cognitive decline (Lin et al. 2013, JAMA Intern Med 173: 293-299).

Currently no approved pharmaceutical treatment exists and recent meta-analysis of the standard-of-care, off-label use of corticosteroid therapy have concluded that neither systemic nor intratympanic administration has any significant treatment effect (Crane et al. 2015, Laryngoscope 125(1):209-17).

Inhibition of the protein phosphatase calcineurin (which mediates neurodegenerative signaling through inflammation, structural degeneration, oxidative stress and programmed cell death pathways after cellular stress and insult) by the immunosuppressive drugs cyclosporine A and tacrolimus has been demonstrated to reduce hearing loss in pre-clinical models of noise-induced hearing loss (Uemaetomari et al. 2005, Hearing Res 209:86-90; Bas et al. 2009, Acta Oto-Laryngologica 129: 385-389) and 2 cases of idiopathic sudden sensorineural hearing loss and autoimmune sudden sensorineural hearing loss (McClelland et al. 2005, Acta Oto-Laryngologica 125: 1356-1360; Di Leo et al. 2011, Acta Otorhinolaryngologica Italica 31:399-401).

However, the use of the approved calcineurin inhibitors (CNIs) cyclosporin A and tacrolimus in transplant medicine is not only immunosuppressive, but also associated with severe adverse effects such as hyperlipidemia, diabetes mellitus, hypertension, nephrotoxicity and neurotoxicity as well as unpredictable individual pharmacokinetics and pharmacodynamics (Naesens & Sarwal 2010, Transplantation 89(11): 1308-1309). While the combination of poor dose-level correlation, unpredictable level-effect association and unclear level-toxicity relation (Naesens et al. 2009, Clin J Am Soc Nephrol 4(2): 481-508) with severe adverse effects resulting in a narrow and individual therapeutic window (necessitating intensive monitoring) may be acceptable in life-threatening conditions such as post-transplant anti-rejection therapy, these characteristics do not render traditional CNIs acceptable drug candidates for the treatment of sensorineural hearing loss.

The inventors surprisingly showed that certain setron family members capable of inhibiting the protein phosphatase calcineurin effectively treated hearing loss in a pre-clinical animal model when administered after acoustic trauma. This treatment effect lead to significant better hearing outcomes than in placebo treated animals and even performed better than a traditional CNI, despite a much lower potency in terms of calcineurin inhibition. The treatment effect was not shared by setron compounds without calcineurin inhibition capacity.

The present invention is therefore directed at the use of calcineurin-inhibiting members of the setron family of compounds as safe and effective therapeutic agents in prophylaxis and treatment of sensorineural hearing loss.

SUMMARY

The present invention thus relates to an inhibitor of calcineurin of the setron family for use for the treatment of hearing loss in a subject in need thereof.

In one embodiment, said inhibitor of calcineurin of the setron family is selected from the group comprising azasetron, tropisetron, ramosetron, ondansetron and analogs and pharmaceutically acceptable salts thereof. Preferably, said inhibitor of calcineurin of the setron family is azasetron or an analog or pharmaceutically acceptable salt thereof.

In one embodiment, the analog of azasetron is a benzoxazine compound of the formula:

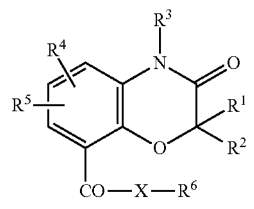

wherein R1 and R2 are the same or different, and each represents hydrogen or $C_{1-8}$ alkyl; R3 represents hydrogen, $C_{1-8}$ alkyl, phenylalkyl or substituted phenylalkyl; R4 and R5 are the same or different, and each represents hydrogen, halogen, $C_{1-8}$ alkyl, alkoxy, amino, acylamino, $C_{2-5}$ alkylamino, hydroxy or nitro; X represents oxygen or NH; R6 represents a group of the formula:

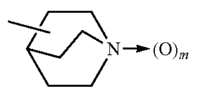

wherein m is 0 or 1, or a group of the formula:

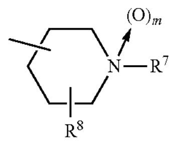

wherein R7 represents $C_{1-8}$ alkyl, phenyl $C_{1-4}$ alkyl, phenoxyalkyl, substituted phenyl $C_{1-4}$ alkyl or substituted phenoxyalkyl, R8 represents hydrogen or $C_{1-8}$ alkoxy and m is as defined above, or a group of the formula:

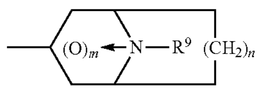

wherein R9 represents $C_{1-8}$ alkyl, phenyl $C_{1-4}$ alkyl or substituted phenyl $C_{1-4}$ alkyl, n is 0 or 1, and m is as defined above, or a pharmaceutically acceptable salt thereof.

In one embodiment, said azasetron analog is selected from the group comprising 6-chloro-3,4-dihydro-2-methyl-3-oxo-N-(3-quinuclidinyl)-2H-1,4-benzoxazine-8-carboxamide, 6-chloro-3,4-dihydro-2,4-dimethyl-3-oxo-N-(3-quinuclidinyl)-2H-benzoxazine-8-carboxamide, 6-chloro-2-ethyl-3,4-dihydro-4-methyl-3-oxo-N-(3-quinuclidinyl)-2H-1,4-benzoxazine-8-carboxamide, 6-chloro-3,4-dihydro-4-methyl-3-oxo-N-(3-quinuclidinyl)-2H-1,4-benzoxazine-8-carboxamide, 6-bromo-3,4-dihydro-2,4-dimethyl-3-oxo-N-(3-quinuclidinyl)-2H-1,4-benzoxazine-8-carboxamide and 6-chloro-3,4-dihydro-2,2,4-trimethyl-3-oxo-N-(3-quinuclidiny-1)-2H-1,4-benzoxazine-8-carboxamide, and pharmaceutically acceptable salts thereof.

In one embodiment, said hearing loss is sensorineural hearing loss.

In one embodiment, said hearing loss is a decrease in hearing of at least about 20, 30, 40, 50, 60, 70, 80, 90 dB or more over at least three contiguous frequencies. In another embodiment, said hearing loss is total deafness.

In one embodiment, said hearing loss is unilateral or bilateral.

In one embodiment, said hearing loss is sudden sensorineural hearing loss.

In one embodiment, said hearing loss is noise induced sensorineural hearing loss or age-related hearing loss.

In one embodiment, said subject is affected with hearing loss since less than 7 days.

In one embodiment, the inhibitor of calcineurin is systemically administered or topically administered or intratympanically injected.

In one embodiment, the inhibitor of calcineurin is administered 1 to 3 times a day.

In one embodiment, the inhibitor of calcineurin is administered for at least 30 days.

DEFINITIONS

In the present invention, the following terms have the following meanings:

"Hearing loss" refers to a hearing loss of at least 10 dB, preferably of at least 20 dB, more preferably of at least 30 dB in three consecutive frequencies on a standard audiogram. Hearing loss may be unilateral (i.e. it impacts only one ear of a subject) or bilateral (i.e. it impacts both ears of a subject).

"Sensorineural hearing loss" refers to a type of hearing loss caused by an abnormality and/or damage to the sensory hair cells and neurons of the cochlea, or of the auditory nerve or higher aspects of central auditory perception or processing. Sensory hair cells and neurons of the cochlea or the auditory nerve may be abnormal at birth or may be damaged during the life time (see below for a list of possible causes of sensorineural hearing loss).

"Treatment" or "treating" refer to both therapeutic treatment and prophylactic or preventative measures; wherein the object is to prevent or slow down (lessen) hearing loss. Those in need of treatment include those already with hearing loss as well as those prone to have hearing loss or those in whom hearing loss is to be prevented. A subject is successfully "treated" for hearing loss if, after receiving a therapeutic amount of a compound according to the present invention, the subject shows observable and/or measurable improved hearing, and/or improvement in quality of life issues. The above parameters for assessing successful treatment and improvement in hearing loss are readily measurable by routine procedures familiar to a physician, such as, for example, by audiometry.

"Therapeutically effective amount" means level or amount of a compound that is aimed at, without causing significant negative or adverse side effects to the target, (1) delaying or preventing the onset of hearing loss; (2) slowing down or stopping the progression, aggravation, or deterioration of hearing loss; (3) bringing about ameliorations of the symptoms of hearing loss; (4) reducing the severity or incidence of hearing loss; or (5) curing hearing loss. A therapeutically effective amount may be administered prior to the onset of hearing loss, for a prophylactic or preventive action. Alternatively or additionally, the therapeutically effective amount may be administered after initiation of hearing loss, for a therapeutic action.

By "pharmaceutically acceptable" is meant that the ingredients of a pharmaceutical composition are compatible with each other and not deleterious to the subject to which it is administered.

A "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

The term "subject" herein refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of a disease.

"Alkyl" refers to any saturated linear or branched hydrocarbon chain, with 1 to 12 carbon atoms, preferably 1 to 8 carbon atoms, and more preferably methyl, ethyl, propyl, isopropyl, butyl, n-butyl, sec-butyl, isobutyl, tert-butyl, pentyl, hexyl, heptyl or octyl.

"Halogen" refers to fluorine, chlorine, bromine or iodine.

"Alkoxy" refers to any —O-alkyl group, wherein alkyl is as defined above. Suitable alkoxy groups include for example methoxy, ethoxy, n-propoxy, isopropoxy, n-butoxy, f-butoxy, sec-butoxy, n-pentoxy, pentyloxy, hexyloxy, heptyloxy or octyloxy.

"Amino" refers to any compound derived from ammoniac $NH_3$ by substitution of one or more hydrogen atoms with an organic radical. Amino preferably refers to $—NH_2$, —NHR and —NRR' wherein R and R' are preferably alkyl groups. Therefore "amino" includes monoalkylamino and dialkyl amino groups.

"Acylamino" refers to the groups —NRC(O)alkyl, —NRC(O)cycloalkyl, —NRC(O)cycloalkenyl, —NRC(O)alkenyl, —NRC(O)alkynyl, —NRC(O)aryl, —NRC(O)heteroaryl and —NRC(O)heterocyclic, wherein R is hydrogen or alkyl. Preferably, "acylamino" refers to $C_{2-5}$ alkanoylamino such as, for example, acetylamino, propionylamino, butyrylamino or pivaloylamino.

"Alkylamino" refers to any —N-alkyl group and includes groups wherein the amino moiety is substituted by mono- or di-alkyl, wherein alkyl is as defined above. Suitable alkylamino groups include, without limitation, methylamino, ethylamino, propylamino, isopropylamino, butylamino, hexylamino, octylamino, dimethylamino, diethylamino, dipropylamino, diisopropylamino, dibutylamino, dihexylamino or dioctylamino.

"Phenylalkyl" refers to a phenyl group comprising an alkyl moiety, preferably said phenylalkyl is a "Phenyl $C_{1-4}$ alkyl", i.e. a group comprising an alkyl moiety bearing 1 to 4 carbon atoms. Suitable phenylalkyl compounds include, but are not limited to, benzyl, 2-phenylethyl, 1-phenylethyl, 3-phenylpropyl and 4-phenylbutyl. Substituent(s) of the phenyl nucleus may be selected from the group comprising 1 to 3 halogen atoms, alkoxy groups, alkyl groups, nitro groups, amino groups, trifluoromethyl groups, carboxy groups and alkoxycarbonyl groups.

"Phenoxyalkyl" refers to a phenoxy group comprising an alkyl moiety, preferably said phenoxyalkyl is a "Phenoxy $C_{1-4}$ alkyl", i.e. a group comprising an alkyl moiety bearing 1 to 4 carbon atoms. Suitable phenylalkyl compounds include, but are not limited to, phenoxymethyl, 2-phenoxyethyl, 3-phenoxypropyl and 4-phenoxybutyl. Substituent(s) of the phenyl nucleus may be selected from the group comprising 1 to 3 halogen atoms, alkoxy groups, alkyl groups, nitro groups, amino groups, trifluoromethyl groups, carboxy groups and alkoxycarbonyl groups.

"About" preceding a figure means plus or less 10% of the value of said figure.

DETAILED DESCRIPTION

The inventors showed (see Examples), that some, but not all, compounds of the setron family act as calcineurin inhibitors. Moreover, these calcineurin inhibitors of the setron family were surprisingly proved to present a therapeutic potential for treating hearing loss.

The present invention thus relates to a method for treating hearing loss in a subject, comprising administering a calcineurin inhibitor of the setron family to a subject.

The present invention also relates to a calcineurin inhibitor of the setron family for treating, or for use in treating, hearing loss in a subject.

The setron family is a family of serotonin 5-HT3 antagonists and includes, without limitation, the following compounds: azasetron, ondansetron, palonosetron, tropisetron, lerisetron, alosetron, granisetron, dolasetron, bemesetron, ramosetron, itasetron, zacopride, and cilansetron.

Methods for determining if a compound of this family is a calcineurin inhibitor are known in the art. An example of such a method is shown in Example 1, and corresponds to the Test A described below.

In one embodiment, the present invention relates to compounds of the setron family capable of inhibiting calcineurin activity in the conditions of Test A.

According to Test A, phosphatase calcineurin activity is assessed in cerebellar granule neurons (CGNs) using a colorimetric assay kit based on quantification of the green complex formed between malachite green, molybdate and free phosphate released. CGNs are detached from plates, for example by scraping, rinsed in ice-cold tris buffer solution (TBS) and counted. About 10 million cells are lysed in 1 ml of the provided lysis buffer and centrifuged at 150,000×g at 4° C. for 45 min, and the supernatant may be stored at −70° C. until analysis. Prior to calcineurin activity assay, free phosphate and nucleotides are removed from cellular extract by gel filtration. To ensure the complete removal of phosphate, malachite green reagent may be added, which will turn the color green in presence of phosphate. A specific calcineurin substrate is added to phosphate-free cellular extracts and after appropriate incubation period, malachite green reagent is applied. The rapid green color formation from the reaction is measured, for example on a spectrophotometer. The developed color is proportional to the calcineurin phosphatase activity of samples. Absorbance values, read at 620 nm, may thus be transformed to percentage calcineurin activity relative to K25 control treatment (100%).

In one embodiment of the invention, the calcineurin inhibitor of the setron family is capable of inhibiting calcineurin activity by at least about 20%, preferably at least about 30, 40, 50, 60, 70, 80% or more when used at a dose of about 10 nM, 50, 100, 200, 300, 400, 500, 600, 700, 800, 900 or 1000 nM. In one embodiment, the calcineurin inhibitor of the setron family is capable of inhibiting calcineurin activity by at least about 50%, preferably at least about 60, 70, 80% or more when used at a dose of about 1000 nM.

In one embodiment, the calcineurin inhibitor of the setron family is selected from the group comprising azasetron, ondansetron, tropisetron, ramosetron, salts, and analogs thereof.

Pharmaceutically acceptable salts of setron compounds that may be used in the present invention are pharmaceutically acceptable acid addition salts, such as, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic, in particular methanesulfonic acid, or aromatic sulfonic acids, for example benzene-, p-toluene- or naphthalene-2-sulfonic acid.

In one embodiment, the calcineurin inhibitor of the setron family is azasetron, ondansetron, or a salt thereof, or an analog thereof.

Preferably, the calcineurin inhibitor of the setron family is azasetron or a salt, or an analog thereof.

Azasetron is 6-chloro-3,4-dihydro-N-(8-methyl-8-azabicyclo-[3.2.1]-oct-3-yl)-2,4-dimethyl-3-oxo-2H-1,4-benzoxazine-8-carboxamide, which may also be referred as N-(1-azabicyclo[2.2.2]octan-8-yl)-6-chloro-4-methyl-3-oxo-1,4-benzoxazine-8-carboxamide.

In one embodiment, an analog of azasetron that may be used in the present invention is an analog of azasetron described in the U.S. Pat. No. 4,892,872, which is incorporated herein by reference.

Analogs of azasetron described in U.S. Pat. No. 4,892,872 are benzoxazine compounds of the formula:

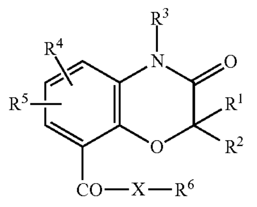

wherein R1 and R2 are the same or different, and each represents hydrogen or $C_{1-8}$ alkyl; R3 represents hydrogen, $C_{1-8}$ alkyl, phenylalkyl or substituted phenylalkyl; R4 and R5 are the same or different, and each represents hydrogen, halogen, (C1-C8) alkyl, alkoxy, amino, acylamino, $C_{2-5}$ alkylamino, hydroxy or nitro; X represents oxygen or NH; R6 represents a group of the formula:

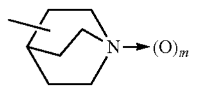

wherein m is 0 or 1, or a group of the formula:

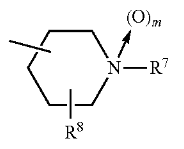

wherein R7 represents $C_{1-8}$ alkyl, phenyl $C_{1-4}$ alkyl, phenoxyalkyl, substituted phenyl $C_{1-4}$ alkyl or substituted phenoxyalkyl, R8 represents hydrogen or $C_{1-8}$ alkoxy and m is as defined above, or a group of the formula:

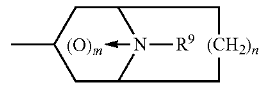

wherein R9 represents $C_{1-8}$ alkyl, phenyl $C_{1-4}$ alkyl or substituted phenyl $C_{1-4}$ alkyl, n is 0 or 1, and m is as defined above, or a pharmaceutically acceptable salt thereof.

Examples of analogs of azasetron include, but are not limited to, 6-chloro-3,4-dihydro-2-methyl-3-oxo-N-(3-quinuclidinyl)-2H-1,4-benzoxazine-8-carboxamide, 6-chloro-3,4-dihydro-2,4-dimethyl-3-oxo-N-(3-quinuclidinyl)-2H-benzoxazine-8-carboxamide, 6-chloro-2-ethyl-3,4-dihydro-4-methyl-3-oxo-N-(3-quinuclidinyl)-2H-1,4-benzoxazine-8-carboxamide, 6-chloro-3,4-dihydro-4-methyl-3-oxo-N-(3-quinuclidinyl)-2H-1,4-benzoxazine-8-carboxamide, 6-bromo-3,4-dihydro-2,4-dimethyl-3-oxo-N-(3-quinuclidinyl)-2H-1,4-benzoxazine-8-carboxamide and 6-chloro-3,4-dihydro-2,2,4-trimethyl-3-oxo-N-(3-quinuclidiny-1)-2H-1,4-benzoxazine-8-carboxamide, and pharmaceutically acceptable salts thereof.

In one embodiment, the present invention relates to the acute treatment of hearing loss. As used herein, the terms "acute treatment of hearing loss" refer to a treatment started as soon as possible after the onset of hearing loss, such as, at most 7 days after the onset of hearing loss. In one embodiment, the treatment starts at most about 1 day, about 2 days, about 3 days, about 4 days, about 5 days, about 6 days or at most about 7 days after the onset of hearing loss.

In one embodiment, the term "onset of hearing loss" may refer to the exposure to the cause of hearing loss (such as, for example, exposure to loud noise for noise-induced hearing loss). In another embodiment, the term "onset of hearing loss" may refer to the diagnosis of hearing loss by a physician. In another embodiment, the term "onset of hearing loss" may refer to the perception by the subject of a loss, preferably of a significant loss, of hearing capacities, or to the perception by the subject of a loss of hearing capacities significantly impacting his/her quality of life.

Acute treatment of hearing loss is of particular interest because it allows preventing chronic hearing loss and tinnitus, as degenerative processes in the cochlea such as oxidative stress and apoptosis are not only initiated directly after an insult, but remain active for up to 4 weeks resulting in continued significant cell death for 2-3 weeks post-insult (Yang et al. 2004, Hearing Res; Yamashita et al. 2004, Brain Res). As significant degeneration and cell death is still ongoing after one week post-insult, treatment initiated at least up to this point has the potential to significantly improve long term outcomes.

In one embodiment, the present invention relates to the chronic treatment of hearing loss, in particular for the treatment of age-induced hearing loss or for the prevention of worsening of age-induced hearing loss. In one embodiment, the term "chronic treatment" means a treatment for an indefinite period of time, such as, for example, for about 1 year, or for about 2, 3, 4, 5, 6, 7, 8, 9, 10, 15, 20 years of more.

In one embodiment, the term "hearing loss" refers to decrease in hearing of at least about 10 dB, or 20, 30, 40, 50, 60, 70, 80, 90 dB or more over at least three contiguous frequencies. In one embodiment, "hearing loss" refers to total deafness.

In one embodiment, hearing loss is bilateral hearing loss, which means that decrease in hearing is observed in both ears of the subject. In another embodiment, hearing loss is unilateral, i.e. only observed in one ear, whereas the hearing capacity of the other stands normal.

Normal hearing range usually is from 20 Hz to 20000 Hz. In one embodiment, hearing loss may affect all sound frequencies. In another embodiment, hearing loss only affects some sound frequencies, such as, for example, hearing loss in the low frequency (such as, for example, up to about 500, 1000 or 2000 Hz, whereas hearing at higher frequencies is normal) or hearing loss in the high frequency (such as, for example, hearing loss beginning at about 4000 Hz, 6000, 8000 or 10000 Hz).

Methods for measuring hearing loss are well-known by the skilled artisan. Examples of such methods include, but are not limited to, tuning fork test, bone conduction test, pure tone audiogram, ABR (auditory brainstem responses) measurement, DPOAE (distortion product otoacoustic emissions) measurement, TEOAE (transiently evoked otoacoustic emissions) measurement, speech in noise test, word comprehension test and the like.

Hearing loss include sensorineural hearing loss, conductive hearing loss and mixed hearing loss (wherein mixed hearing loss is a combination of both sensorineural and conductive hearing loss).

Conductive hearing loss results from abnormalities of the external ear, tympanic membrane, middle ear space or ossicles. It may results from cerumen impaction, middle ear fluid, otitis media, foreign bodies, perforated tympanic membrane, canal edema from otitis externa, otosclerosis, trauma or cholesteatoma (all these conditions may be diagnosed by otoscopy).

Sensorineural hearing loss and conductive hearing loss may be distinguished according to tests well known of the skilled artisan, including, without limitation, Weber and Rinne tests, otoscopy and audiometry.

In one embodiment, hearing loss is sensorineural hearing loss or mixed hearing loss, preferably sensorineural hearing loss.

In one embodiment, hearing loss is not conductive hearing loss, or does not include conductive hearing loss.

In one embodiment, hearing loss is sudden hearing loss (SHL). Sudden hearing loss may be defined by the following audiometric criterion: decrease in hearing of at least about 10 dB, 20 dB, 30 dB or more over at least three contiguous frequencies, evolving within 3 days or less. Because premorbid audiometry is generally unavailable, for unilateral hearing loss, hearing loss may be defined as related to the opposition ear's thresholds.

In a particular embodiment, hearing loss is sudden sensorineural hearing loss (SSNHL).

Sudden hearing loss, preferably SSNHL, may result (without limitation) from vestibular schwannoma (acoustic neuroma), stroke, malignancy, vascular ischemia of the inner ear, perilymph fistula or autoimmune causes (including, without limitation, IgE or IgG allergy) or other causes (such as, for example, causes listed below). However, a cause of SSNHL is identified in only 10 to 15% of patients at the time of presentation.

In one embodiment, sudden hearing loss, preferably SSNHL is idiopathic, which means that no cause was identified despite adequate investigation.

Examples of causes of sensorineural hearing loss include, but are not limited to, excessive noise exposure (such as, for example, exposure to a noise of more than about 70 dB, 80 dB, 90 dB, 100 dB, 110 dB, 120 dB, 130 dB or more), aging, inner ear involvement by infectious agents (such as, for example, viral and bacterial infections), autoimmunity (such as, for example, autoimmune inner ear disease) or vasculopathy, illnesses (including but not limited to high blood pressure and diabetes), ototoxic drugs, head trauma, tumors or blast exposure.

In one embodiment, hearing loss, preferably sensorineural hearing loss, is congenital, i.e. sensory hair cells and neurons of the cochlea or the auditory nerve were abnormal at birth. Examples of causes of congenital hearing loss, preferably congenital sensorineural hearing loss include, but are not limited to, a lack of development (aplasia) of the cochlea, chromosomal syndromes, congenital cholesteatoma, delayed familial progressive, congenital rubella syndrome, and human Cytomegalovirus (HCMV) transmission to a developing fetus during pregnancy.

In another embodiment, hearing loss, preferably sensorineural hearing loss, is acquired, i.e. sensory hair cells and neurons of the cochlea or the auditory nerve were normal at birth, but were subsequently damaged.

Examples of causes of acquired hearing loss, preferably acquired sensorineural hearing loss include, but are not limited to, inflammatory causes, ototoxic drugs, physical trauma (such as, for example, a head injury, a fracture of the temporal bone affecting the cochlea and middle ear, or a shearing injury affecting cranial nerve VIII), noise exposure, presbycusis, tumors or diseases.

Examples of inflammatory causes of sensorineural hearing loss include, but are not limited to, autoinflammatory diseases (such as, for example, Muckle-Wells Syndrome), suppurative labyrinthitis, meningitis, mumps or measles.

Examples of viral causes of sensorineural hearing loss include, but are not limited to, syphilis, mumps or measles.

Examples of ototoxic drugs that may cause sensorineural hearing loss include, but are not limited to, aminoglycosides (such as, for example, tobramycin), chemotherapeutic agents (such as, for example, platinum drugs, including, without limitation, cisplatin, carboplatin, oxaliplatin, satraplatin, picoplatin, tetraplatin, transplatin, nedaplatin, ormaplatin, PtCl2[R,RDACH], pyriplatin, ZD0473, BBR3464 and Pt-1C3), loop diuretics (such as, for example, furosemide), antimetabolites (such as, for example, methotrexate) and salicylates (such as, for example, aspirin).

Presbycusis refers to hearing loss that typically, but not only, occurs in the high frequency range (4000 Hz to 8000 Hz), mainly in the elderly. It is considered by some to be a degenerative process, although there has never been a proven link to aging.

Examples of tumors that may induce sensorineural hearing loss include, but are not limited to, cerebellopontine angle tumour, such as, for example, acoustic neuroma and meningioma.

A non-limiting example of disease leading to sensorineural hearing loss is Meniere's disease. It typically, but not only, causes sensorineural hearing loss in the low frequency range (125 Hz to 1000 Hz). In one embodiment of the invention, sensorineural hearing loss does not result from or is not associated with Meniere's disease.

Other examples of causes of sensorineural hearing loss include, but are not limited to, autoimmune diseases (such as, for example, granulomatosis with polyangiitis), adenoids that do not disappear by adolescence resulting in obstruction of the Eustachian tube, causing conductive hearing impairment and nasal infections that can spread to the middle ear, AIDS, ARC, HIV (and subsequent opportunistic infections), chlamydia, fetal alcohol syndrome, premature birth, otosclerosis, posterior circulation infarct and Charcot-Marie-Tooth disease.

In one embodiment, hearing loss, preferably sensorineural hearing loss, is inherited, for example, it results from a genetic predisposition of the subject. More than 40 genes have been identified to cause deafness, including, without limitation, DFNB1 (also known as Connexin 26 or GJB) and MT-TL1. Examples of syndromes resulting in hearing loss include, but are not limited to, Stickler syndrome, Waardenburg syndrome, Pendred syndrome, large vestibular aqueduct syndrome and Usher syndrome.

In one embodiment, sensorineural hearing loss is idiopathic, i.e. without identified cause.

In one embodiment, sensorineural hearing loss is noise-induced sensorineural hearing loss. Hearing loss may for example be induced by exposure to loud noises (such as, for example, of more than about 90 dB, 100 dB, 110 dB, 120 dB, 130 dB or more), or by prolonged exposure to less loud noises. Indeed, the louder the noise, the shorter the safe amount of exposure. For example, the safe daily exposure amount at 85 dB is of about 8 hours, while it is of only 2 hours at 91 dB.

In one embodiment, sensorineural hearing loss is age-induced sensorineural hearing loss. Therefore, in one embodiment, the subject to be treated according to the present invention is at least 30, 40, 50, 60, 70, 80 years old or more.

In one embodiment, the subject receiving the setron compound of the invention experiences hearing loss for at least 24 hours, i.e. according to this embodiment, subjects with only temporary hearing loss are excluded from the scope of the present invention.

Therefore, in one embodiment, the subject starts receiving the treatment of the invention between about 24 hours and about 7 days after the onset of hearing loss. In one embodiment, the subject starts receiving the treatment of the invention between about 24 hours and about 2, 3, 4, 5 or 6 days after the onset of hearing loss. According to this embodiment, the term "acute treatment of hearing loss", may thus refer to a treatment beginning between about 24 hours and about 2, 3, 4, 5, 6 or 7 days after hearing loss onset.

In one embodiment, the subject is at risk of hearing loss. Examples of risk of hearing loss include, but are not limited to, genetic predisposition to hearing loss, familial history of hearing loss, history of previous episodes of hearing loss, noise exposure, exposure to ototoxic agent (including, without limitation, ototoxic drugs), aging and the like.

In one embodiment, the compound of the invention may be administered prior to the onset of hearing loss, such as, for example, prior to the exposure to a noise or agent that may cause hearing loss. As used herein, when the compound of the invention is used for treating or preventing noise-induced hearing loss, "prior to" may refer to an administration a few hours or minutes before exposition to noise. In another embodiment, the compound of the invention may also be administered during or after the exposure to a noise or agent that may cause hearing loss, such as, for example, a few minutes or hours after.

In another embodiment, the compound of the invention may be administered to diminish ongoing age-related hearing loss. As used herein, when the compound of the invention is used for treating or preventing age-related hearing loss, "prior to" refers to administration after the risk of, or beginning of, age related hearing loss has been determined, but prior to its continued worsening.

In one embodiment, the subject is a child or an adolescent. In another embodiment, the subject is an adult, i.e. a subject of at least about 18 or 20 years old or more. In another embodiment, the subject is at least 30, 40, 50, 60, 70, 80 years old or more.

In one embodiment, the subject is a male. In another embodiment, the subject is a female.

In one embodiment, the subject is not affected and/or diagnosed with a vestibular disease, i.e. labyrinthine, vestibular nerves or vestibuli nuclei diseases responsible of vestibular dysfunction. Examples of vestibular diseases include, but are not limited to, vertigo (such as, for example, benign paroxysmal vertigo and familial episodic vertigo), vestibular neuritis, Meniere's disease (such as, for example, chronic Meniere's disease), endolymphatic hydrops, perilymphatic fistula, vestibular disorders resulting from head trauma, labyrinthine haemorrhage, chronic or acute labyrinthine (such as, for example, of viral, immune or bacterial origin), serous labyrinthine, barotraumatism of the vestibule, autoimmune inner ear disease, vestibular migraine, migraine associated with vestibular syndromes, vestibular syndromes resulting from chirurgical treatment of the middle ear, middle ear tumor, endolymphatic sac tumor, pontocerebellar angle tumor, cerebellopontine or temporal bone tumors involving the vestibular nerves and/or the labyrinth, brainstem tumors or lesions associated with vestibular disorders (such as, for example, multiple sclerosis, stroke or angeitis), inner ear channelopathies, vestibular schwannomas, presbyvestibulia and the like. In one embodiment, the subject is not affected with acute vestibular dysfunction (such as, for example, barotraumatism, Menière's disease or migraine associated vertigo). In another embodiment, the subject is not affected with chronic vestibular dysfunction (such as, for example, sequellae from acute vestibular dysfunction or presbyvestibulia).

In another embodiment, the subject does not present any vestibular damage or vestibular lesion. Examples of lesional vestibular disorder include but are not limited to vestibular neuritis, viral neuronitis, labyrinthitis, viral endolymphatic labyrinthitis, drug-induced ototoxicity, Ménière's disease, endolymphatic hydrops, head trauma with lesional vestibular deficits, labyrinthine haemorrhage, chronic or acute labyrinthine infection, serous labyrinthine, barotraumatism, autoimmune inner ear disease, presbyvestibulia and toxic vestibular impairments.

In another embodiment, the subject is not affected by tinnitus.

The present invention also relates to a composition comprising or consisting of a calcineurin inhibitor of the setron family as described hereinabove.

The present invention also relates to a pharmaceutical composition comprising or consisting of or consisting essentially of a calcineurin inhibitor of the setron family as described hereinabove in combination with at least one pharmaceutically acceptable excipient.

The present invention also relates to a medicament comprising or consisting of or consisting essentially of a calcineurin inhibitor of the setron family as described hereinabove.

The present invention further relates to a nutraceutical composition comprising or consisting of or consisting essentially of an inhibitor of calcineurin of the setron family, as described hereinabove. In particular, the present invention also relates to a nutraceutical composition of the invention for treating age-related hearing loss in a subject in need thereof.

As used herein, the term "consisting essentially of", with reference to a pharmaceutical composition or medicament or nutraceutical composition of the invention, means that the at least one inhibitor of calcineurin of the setron family is the only one therapeutic agent or agent with a biologic activity within said pharmaceutical composition or medicament or nutraceutical composition.

In the composition, pharmaceutical composition, medicament or nutraceutical composition of the invention, the setron compound, alone or in combination with another active principle, can be administered in a unit administration form, as a mixture with conventional pharmaceutical supports, to a subject. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal, intra-tympanic and intranasal administration forms and rectal administration forms.

Preferably, the composition, pharmaceutical composition, medicament or nutraceutical composition contains vehicles which are pharmaceutically acceptable for a formulation capable of being injected, preferably systemically or intratympanically injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. In one embodiment, the composition, pharmaceutical composition, medicament or nutraceutical composition is in the form of a gel.

In one embodiment, the composition, pharmaceutical composition, medicament or nutraceutical composition comprises sustained-release matrices, such as biodegradable polymers.

Examples of pharmaceutical forms suitable for injectable use include, but are not limited to, sterile aqueous solutions or dispersions; gel formulation; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising a setron compound of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The setron compound of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions may be prepared by incorporating the setron compound in the required amount in the appropriate solvent with one or several of the other ingredients enumerated in the present invention, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion. Some variation in dosage will necessarily occur depending on the condition of the subject being treated.

The person responsible for administration will, in any event, determine the appropriate dose for the individual subject. The setron compound of the invention may be formulated within a therapeutic mixture to comprise about 0.01 to 1000 milligrams, preferably from about 1 to 400 milligrams, more preferably from about 5 to 100 mg per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In one embodiment, a therapeutically effective amount of said calcineurin inhibitor of the setron family is administered to the subject.

In one embodiment, the therapeutically effective amount ranges from about 1 to about 10000 mg/ml of the setron compound of the invention, preferably 50 to about 5000 mg/ml, more preferably from about 200 to about 2000 mg/ml of the setron compound of the invention. In one embodiment, the therapeutically effective amount ranges from about 1 to about 10000 mg/ml of the setron compound of the invention, preferably 2 to about 2000 mg/ml, more preferably from about 5 to about 500 mg/ml of the setron compound of the invention.

In one embodiment, the therapeutically effective amount ranges from about 1 to about 10000 mg/g of the setron compound of the invention, preferably 50 to about 5000 mg/g, more preferably from about 200 to about 2000 mg/g of the setron compound of the invention. In another embodiment, the therapeutically effective amount ranges from about 1 to about 10000 mg/g of the setron compound of the invention, preferably 2 to about 2000 mg/g, more preferably from about 5 to about 500 mg/g of the setron compound of the invention.

It will be understood that the total daily usage of the setron compound of the invention, composition, pharmaceutical composition, medicament or nutraceutical composition of the present invention will be decided by the attending physician within the scope of sound medical judgment. The specific therapeutically effective dose level for any particular patient will depend upon a variety of factors including the hearing loss being treated and the severity of the hearing loss; activity of the specific setron compound employed; the specific composition employed, the age, body weight, general health, sex and diet of the subject; the time of administration, route of administration, and rate of excretion of the specific setron compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the setron compounds may be varied over a wide range from about 0.01 to 500 mg per adult per day. In another embodiment, the daily dosage of the setron compounds may be varied over a wide range from about 1 to 10000 mg per adult per day, preferably from about 2 to about 2000 mg per adult per day, more preferably from about 5 to about 500 mg per adult per day. Preferably, the compositions contain about 0.01, 0.05, 0.1, 0.5, 1.0, 2.5, 5.0, 10.0, 15.0, 20.0, 25.0, 50.0, 100, 150, 200, 250, 300, 350, 400, 450, 500 mg, 1000 or 2000 mg of the active ingredient for the symptomatic adjustment of the dosage to the patient to be treated. A medication typically contains from about 0.01 mg to about 500 mg of the active ingredient, preferably from 1 mg to about 100 mg of the active ingredient. In one embodiment, the composition of the invention contains from about 1 mg to about 10000 mg of the active ingredient, preferably from about 2 mg to about 2000 mg, more preferably from about 5 mg to about 500 mg of the active ingredient. The composition of the invention may comprise the setron compound in a range of about 1 mg to about 100 mg, preferably from about 5 mg to about 20 mg, more preferably of about 10 mg. The composition of the invention may also comprise the setron compound in a range of about 1 mg to about 10000 mg, preferably from about 2 mg to about 2000 mg, more preferably from about 5 mg to about 500 mg. An effective amount of the drug is ordinarily supplied at a dosage level from about 0.01 mg/kg to about 2 mg/kg of body weight per day, especially from about 0.05 mg/kg to about 0.4 mg/kg of body weight per day, more preferably of about 0.1-0.3 mg/kg of body weight per day.

In one embodiment, an effective amount of the setron compound is supplied at a dosage level from about 0.01 mg/kg to about 100 mg/kg of body weight per day, especially from about 0.02 mg/kg to about 20 mg/kg of body weight per day, more preferably of about 0.05 mg/kg to about 5 mg/kg of body weight per day.

In one embodiment, the compound of the invention is (or is to be) topically administered, preferably is topically applied on the outer ear or on the ear canal. Examples of formulations adapted to topical administration include, but are not limited to, ear drops, solutions or topical gels.

In one embodiment, the compound of the invention is intra-tympanically injected. Examples of formulations adapted to intra-tympanic injection include, but are not limited to, solutions, such as, for example, sterile aqueous solutions, gels, dispersions, emulsions, suspensions, solid forms suitable for using to prepare solutions or suspensions upon the addition of a liquid prior to use, such as, for example, powder, liposomal forms and the like.

In a preferred embodiment, the setron compound of the invention is (or is to be) systemically administered, such as, for example, orally administered, intranasally administered or injected (including, for example, intraperitoneal, intravenously, subcutaneously or intramuscularly injected).

In one embodiment, the setron compound, the composition, the pharmaceutical composition, the medicament or the nutraceutical composition of the invention is (or is to be) orally administered. Examples of forms adapted for oral administration include, but are not limited to, tablets, orodispersing/orally disintegrating tablets, effervescent tablets, powders, granules, pills (including sugarcoated pills), dragees, capsules (including soft gelatin capsules), syrups, liquids, gels or other drinkable solutions, suspensions, slurries, liposomal forms and the like.

In one embodiment, the setron compound, the composition, the pharmaceutical composition, the medicament or the nutraceutical composition of the invention is injected. Therefore, according to this embodiment, the setron compound, the composition, the pharmaceutical composition, the medicament or the nutraceutical composition of the invention is in a form adapted for injection, such as, for example, for intramuscular, subcutaneous, intradermal, transdermal or intravenous injection or infusion. Examples of forms adapted for injection include, but are not limited to, solutions, such as, for example, sterile aqueous solutions, gels, dispersions, emulsions, suspensions, solid forms suitable for using to prepare solutions or suspensions upon the addition of a liquid prior to use, such as, for example, powder, liposomal forms and the like.

In one embodiment, the nutraceutical composition of the invention is (or is to be) orally administered to the subject. Examples of forms adapted for oral administration include, but are not limited to, tablets, orodispersing/orally disintegrating tablets, effervescent tablets, powders, granules, pills (including sugarcoated pills), dragees, capsules (including soft gelatin capsules), syrups, liquids, gels or other drinkable solutions, suspensions, slurries, liposomal forms and the like. In one embodiment, the nutraceutical composition of the invention is in the form of a food additive, drink additive, dietary supplement or nutritional product.

In one embodiment, the setron compound of the invention is administered, or is for administration, three times a day, twice a day, once a day, once every 2 days, once every 3 days, twice a week, once a week or less, preferably, the setron compound of the invention is administered one to three times a day.

In one embodiment, the setron compound is administered, or is for administration, for a period of time of about 1 week, or of about 2, 3, 4, 5, 6, 7, 8 weeks or more, or of about 1, 2, 3, 4, 5, 6, 7, 8, 9, 10, 11, 12 months or more. In one embodiment, the setron compound is administered, or is for administration, until normal hearing, or until the subject recovered about 50%, 60, 70, 80, 90% or more of his hearing capacity. Recovering of the hearing capacity may be measured by methods well known by the skilled artisan, including, without limitation, tuning fork test, bone conduction test, pure tone audiogram, ABR (auditory brainstem responses) measurement, DPOAE (distortion product otoacoustic emissions) measurement, TEOAE (transiently evoked otoacoustic emissions) measurement, speech in noise test, word comprehension test and the like.

In one embodiment, the method of the invention consists in administering a setron compound according to the present invention, which means that the setron compound of the invention is the only one therapeutic compound administered to the subject for treating hearing loss.

In another embodiment, the setron compound may be administered in combination with another therapeutic compound for treating hearing loss, including, without limitation, sodium thiosulfate, vasodilators, magnesium, acetyl-L-carnitine (ALCAR), n-Avetyl-Cysteine (NAC), ebselen, D-methionine, anti-oxidants and ROS scavengers, gingko biloba, glutamate receptor antagonists, JNK kinase inhibitors, alpha lipoic acid, prostaglandin agonists, steroids, vitamin E, A and/or C and the like. In one embodiment, the setron compound and the additional therapeutic compound are administered simultaneously or sequentially.

The present invention further relates to a method for improving hearing in a subject in need thereof, wherein said method comprises or consists in administering a calcineurin inhibitor of the setron family to the subject. Preferably, a therapeutically effective amount of the calcineurin inhibitor of the setron family is administered to the subject.

In one embodiment, the subject is affected by, preferably is diagnosed with, hearing loss, preferable sensorineural hearing loss, more preferably noise-induced sensorineural hearing loss or age-related sensorineural hearing loss.

In one embodiment, the improvement of hearing capacities may correspond to a decreased ABR threshold and/or to an increased DPOAE amplitude.

The present invention further relates to a method for reducing loss of outer hair cells in the cochlea in a subject in need thereof, wherein said method comprises administering a calcineurin inhibitor of the setron family to the subject. Preferably, a therapeutically effective amount of the calcineurin inhibitor of the setron family is administered to the subject.

In one embodiment, the loss of outer hair cells may be induced by an acoustic trauma, such as, for example, loud noise exposure, aging, illnesses (including but not limited to high blood pressure and diabetes), ototoxic drugs, head trauma, tumors, blast exposure, autoimmune inner ear disease, idiopathic causes, viral or bacterial infections.

EXAMPLES

Figure 1:
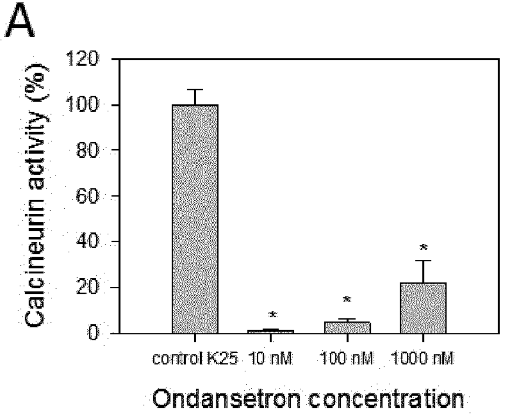
FIG. 1 is a set of histograms showing the effect of setron compound application on calcineurin phosphatase activity after 4 DIV. (A) Ondansetron, (B) Granisetron, (C) Tropisetron, (D) Ramosetron and (E) Azasetron. * signifies $p \leq 0.05$.
Figure 1:
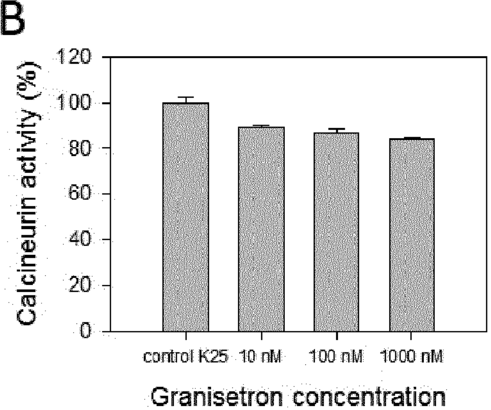
Figure 1:
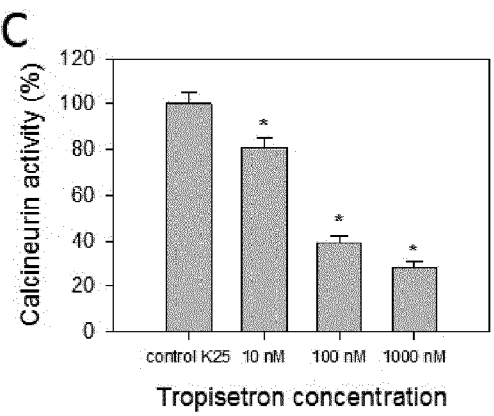
Figure 1:
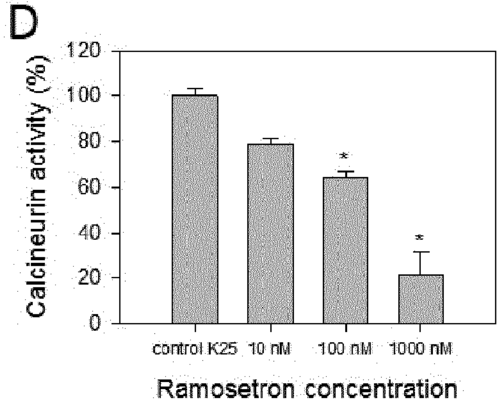
Figure 1:
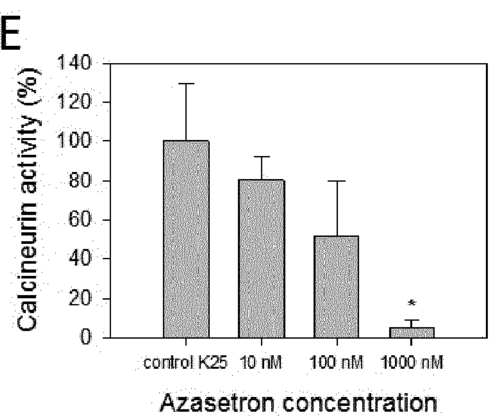

The present invention is further illustrated by the following examples.

Example 1: In Vitro Inhibition of Calcineurin Activity by Setron Compounds

Cell Culture

Cerebellar granule cells were dissociated from the cerebellae of 7-day-old Wistar rat pups as described (Kramer et al. 2003, Mol Cell Neurosci 23:325-330). Briefly, the cerebellae were removed, rinsed in HBSS-BSA, minced, digested with 0.025% trypsin and incubated at 37° C. for 15 min. To stop the digestion, DMEM containing 10% fetal calf serum was added; then a single cell suspension was obtained through pipetting up and down the sedimented tissue. Following centrifugation, cells were counted using trypan blue exclusion test in a Burker chamber. This method is based on the ability of viable cells to exclude trypan blue due to their intact cell membranes, leaving them unstained while non-viable cells take up the dye. Cells at $3.2\times10^5/cm^2$ were seeded in DMEM Hepes modification supplemented with 10% fetal calf serum, 100 μg/ml pyruvate, and 100 μg/ml gentamicin on Polystyrene 12-well tissue culture plates (CELLSTAR) coated with poly-L-lysine. After 24 h, 10 μM cytosine arabinofuranoside was added to inhibit the growth of non-neuronal cells. All pharmacological interventions begun at this time in the culture medium containing 25 mM KCl (K25), which caused depolarization of granule cells and consequently activated gene expression machinery. Moreover, the viability of granule neurons was higher in this milieu and therefore provides the possibility to maintain cells for several days. Indeed, 25 mM KCl is required in the medium for CGN cultures to maintain adequate calcineurin activity and cell maturation and depolarization (Kramer et al., 2003, Mol Cell Neurosci 23:325-330; Vallano et al. 2006, Neuropharmacology 50: 651-660).

Cultures received simple medium (K25 control) or medium containing a setron compound in HCl salt form (Tocris Bioscience, Bristol, UK) at concentrations of 10 nM, 100 nM or 1000 nM for 4 days in vitro (DIV).

Calcineurin Activity Assay

Phosphatase calcineurin activity was assessed in CGNs using a colorimetric assay kit based on quantification of the green complex formed between malachite green, molybdate and free phosphate released. CGNs were detached from plates by scraping, rinsed in ice-cold tris buffer solution (TBS) and counted. About 10 million cells are lysed in 1 ml of the provided lysis buffer and centrifuged at 150,000×g at 4° C. for 45 min, and the supernatant was stored at −70° C. until analysis. Prior to calcineurin activity assay, free phosphate and nucleotides were removed from cellular extract by gel filtration. To ensure the complete removal of phosphate, malachite green reagent was added, which will turn the color green in presence of phosphate. A specific calcineurin substrate was added to phosphate-free cellular extracts and after appropriate incubation period, malachite green reagent was applied. The rapid green color formation from the reaction was measured on a spectrophotometer. The developed color is proportional to the calcineurin phosphatase activity of samples. Absorbance values, read at 620 nm, were transformed to percentage calcineurin activity relative to K25 control treatment (100%). For every single treatment, five independent cultures are assessed and each sample run in triplicate.

Statistics

Statistical analysis was performed using One-way ANOVA followed by Tukey post-hoc test for multiple comparisons. Results are given as mean±SD and a p value less than or equal to 0.05 considered significant.

Results

As shown in FIG. 1, ondansetron HCl, tropisetron HCl, ramosetron HCl and azasetron HCl all significantly inhibited calcineurin phosphatase activity, while granisetron HCl had no effect. For ondansetron HCl and tropisetron HCl, the calcineurin inhibition was significant from 10-1000 nM, for ramosetron HCl at 100 and 1000 nM while the calcineurin inhibitory effect of azasetron HCl only reached significance at 1000 nM due to increased variability of both control and test conditions for this particular assay run. Calcineurin inhibition increased to different degree with increasing concentrations of tropisetron HCl, ramosetron HCl and azasetron HCl while it conversely decreased with increasing concentration of ondansetron HCl. This demonstrates that calcineurin inhibition by setron family compounds is compound specific and not a class effect.

Example 2: In Vivo Treatment of Acoustic Trauma Induced Hearing Loss by Setron Compounds Animals All experiments were performed using 7 week old male Wistar rats (CERJ, Le Genest, France) in accordance with the French Ministry of Agriculture regulations and European Community Council Directive no. 86/609/EEC, OJL 358. The rats were fed a standard diet ad libitum and maintained on a 12 h light-dark cycle.

Audiometry

Auditory Brainstem Reponses (ABR) and Distortion Product Otoacoustic Emissions (DPOAE) were recording using a RZ6 Auditory Workstation (Tucker-Davis Technologies, Alachua, FL, USA) with animals deeply anesthetized using 90 mg/kg ketamine and 10 mg/kg xylazine and placed on a 35° C. recirculating heating pad inside a sound attenuating cubicle (Med Associates Inc., St. Albans, VT, USA) throughout the experiment.

For ABR recordings, three stainless steel needle electrodes were placed subdermally over the vertex, the right mastoid and right hind leg of each animal. Tone-pips (5 msec duration presented at a rate of 21/s) at 8, 16 and 24 kHz were delivered to the right ear using a calibrated MF-1 speaker in closed-field configuration (Tucker-Davis Technologies, Alachua, FL, USA) at attenuating intensity until no reproducible response could be recorded. Close to the ABR threshold, the responses to 1000 acoustic stimuli in 5 dB steps were averaged. Responses were low-pass filtered at 3 kHz.

DPOAEs were recorded and using ER10B+ Low Noise DPOAE microphone (Etymotic Research, Inc., Elk Grove Village, IL, USA) with acoustic stimuli delivered by two calibrated MF-1 speakers in closed-field configuration (Tucker-Davis Technologies, Alachua, FL, USA). DPOAEs were recorded at fixed stimulus levels (L1=L2=70 dB SPL), with an f2/f1 ratio of 1.2. Responses were recorded at 4, 8, 16, 24 and 32 kHz.

Acoustic Trauma

Animals were exposed to 121 dB octave band noise (8-16 kHz) for 2 h in groups of 4 rats, placed in individual compartments of a custom built circular cage placed on a 30 cm diameter platform rotating at 3 turns/minute (Aqila Innovation, Valbonne, France). The calibrated octave band noise generated by the RZ6 SigGen software was further amplified by a Crown D-75 amplifier in bridge mode (Crown Audio, Elkhart, IN, USA) and delivered by four Beyma CP16 compression tweeters (Acustica Beyma S. L., Moncada, Valencia, Spain) positioned 39 cm above the rotating platform, each 10 cm from the platform center.

Drug Treatment

Animals were treated by intraperitoneal injection daily for 14 days beginning immediately after acoustic trauma induction and subsequently repeated every 24 hours. The setron compounds granisetron HCl, ondansetron HCl, tropisetron HCl and azasetron HCl (Tocris Bioscience, Bristol, UK) were delivered dissolved in saline solution (1.6 mL/kg) while Tacrolimus (Selleck Chemicals, Houston, TX, USA) was dissolved in solution composed of 10% ethanol-100%/10% Kolliphor EL/1% Tween 80/79% saline (1.0 mL/kg). Placebo treated animals received injections of 1.6 mL/kg saline following the same treatment schedule.

Histology

After audiometry on day 14, animals were deeply anaesthetized with an intraperitoneal injection of pentobarbital (100 mg/kg). The cochleae were removed, fixed with 4% paraformaldehyde, pH 7.4, decalcified with 10% EDTA, pH 7.4 and then stained with myosin VIIa 1/1000. Inner and outer hair cells (IHCs and OHCs) were observed with the aid of a Zeiss AxioImager Z1/Apotome (Zeiss, France) and counted in 0.20 mm long segments of sensory epithelium from the apex to the base to obtain a cochleogram. The mean loss of OHCs per group was subsequently calculated as a function of normalized distance from the apex in bins of 2.5% of the total length, using the total length of each histological specimen. Cell counts could reliably be obtained for up to 90% of the total distance from the apex (corresponding to the tonotopic region up to from 0 kHz to ~50 kHz in rat, Viberg & Canlon 2004), while the last 10% was too variable due to damage incurred during dissection.

Statistics

Statistical analysis was performed using two-way ANOVA (Audiometry data: frequency and treatment group. Cochleograms: normalized distance from apex and treatment group) followed by Holm-Sidak post-hoc test for multiple comparisons. Results are given as mean±SEM and a p value less than or equal to 0.05 considered significant.

Results

The capacity of three calcineurin inhibiting setron compounds (azasetron HCl, 4.22 mg/kg, ondansetron HCl, 4 mg/kg and tropisetron HCl, 3.5 mg/kg) and one setron compound with no calcineurin inhibition effect (granisetron HCl, 3.8 mg/kg) to reduce hearing loss after acoustic trauma at equimolar doses were compared to the effect of a reference calcineurin inhibitor (Tacrolimus, 1.5 mg/kg) under randomized and placebo controlled conditions. Baseline line audiometry (ABR and DPOAE measures) was performed for each animal 3 days before acoustic trauma was induced. Subsequently, audiometry measures were repeated 24 h and 14 days after acoustic trauma.

Figure 2:
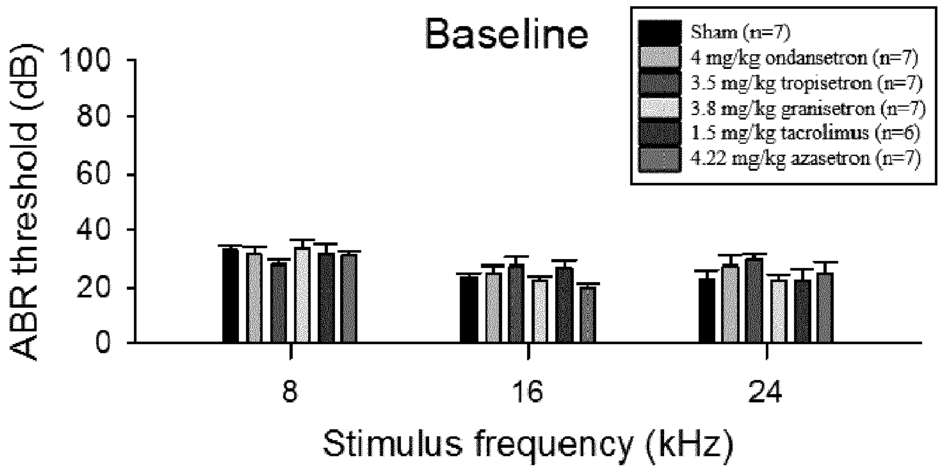
FIG. 2 is a set of histograms showing the auditory brainstem response (ABR) thresholds recorded for the 6 treatment groups at baseline (A), 24 hours after acoustic trauma induction (B) and 14 days after acoustic trauma (C).
Figure 2:
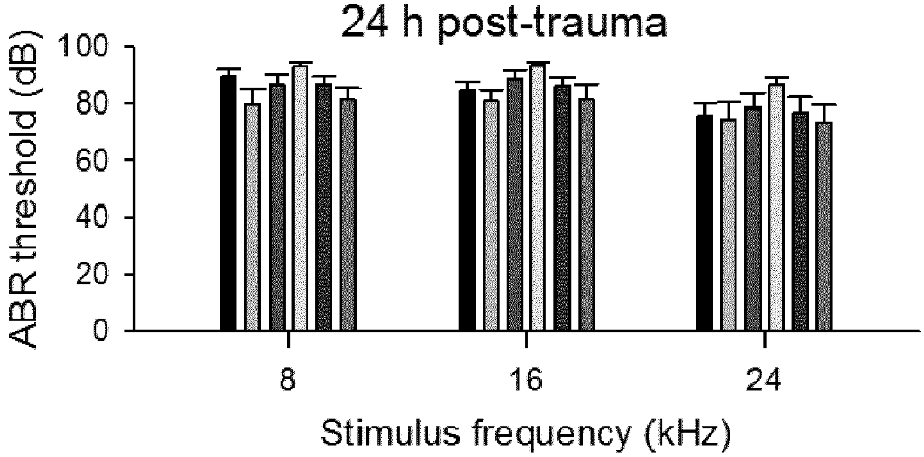
Figure 2:
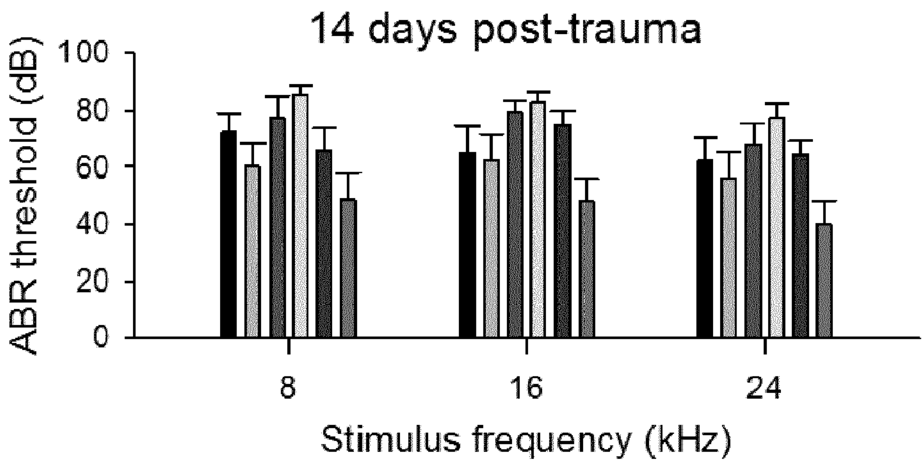
Figure 3:
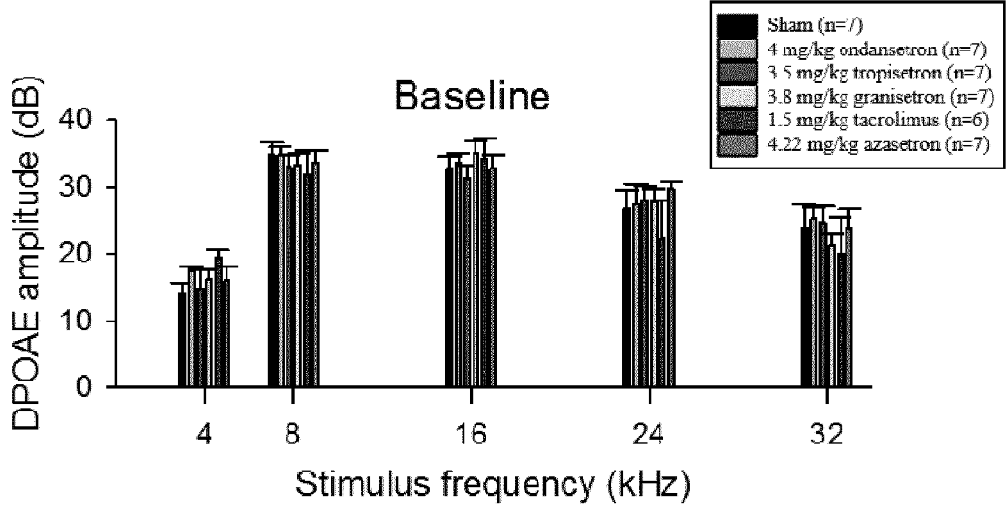
FIG. 3 is a set of histograms showing the distortion product otoacoustic emissions (DPOAEs) amplitudes determined for the 6 treatment groups at baseline (A), 24 hours after acoustic trauma induction (B) and 14 days after acoustic trauma (C).
Figure 3:
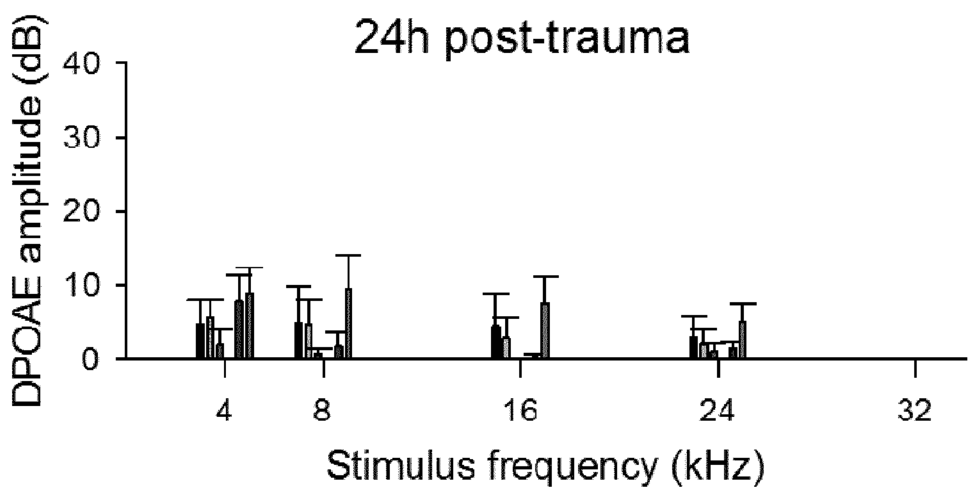
Figure 3:
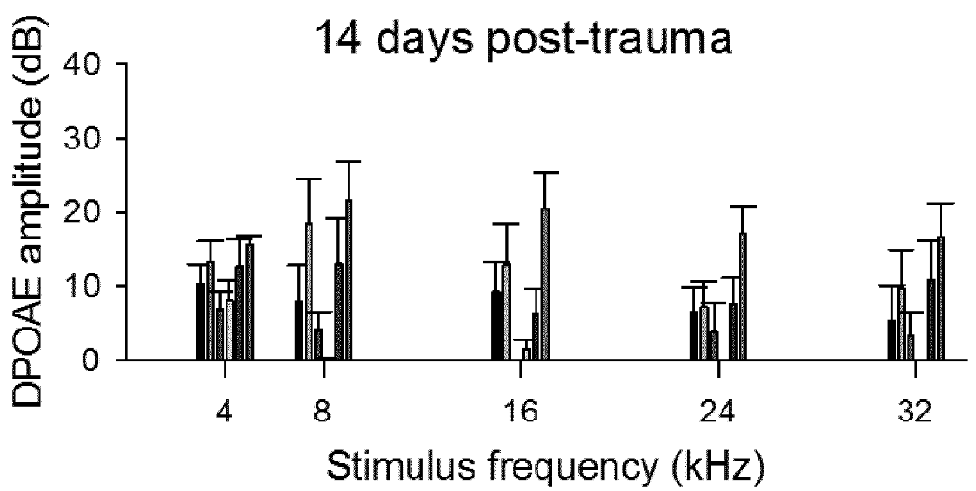

FIGS. 2 & 3 illustrate the audiometry measures (ABR thresholds and DPOAE amplitudes) determined for all treatment groups at baseline, 24 h and 14 days after acoustic trauma. For ABR thresholds exceeding 90 dB, a maximal value of 95 dB was attributed. Following baseline audiometry, a strong positive ABR threshold shift (up to ~70 dB) was seen for all groups accompanied by a severe DPOAE amplitude loss across all frequencies, signifying strongly reduced auditory signal transmission and reduction of outer hair cell amplificatory function. At 14 days after acoustic trauma, auditory function are differentially improved among treatment groups and across frequencies: ABR thresholds improved by ~7-33 dB and DPOAE amplitudes by ~0-17 dB. Compared to placebo treated animals, the group treated with azasetron HCl tendentially showed better hearing outcomes across all frequencies and the tacrolimus and ondansetron HCl treated group showed improvement at some frequencies, while the granisetron HCl or tropisetron HCl treated groups tendentially had both worse ABR thresholds and DPOAE amplitudes than the placebo group. Note that out of 11 tacrolimus treated animals, 5 died between treatment initiation and end of the study (only 6 animals completed the study) while only 2 animals out of 30 were lost for the 5 other groups combined (due to anesthesia complications). This further underscores the potential for adverse effects following repeated treatment with classic calcineurin inhibitors.

To quantify and compare the difference in treatment effects between groups while taking into account individual baseline and trauma variability, the hearing loss (ABR threshold shift & DPOAE amplitude loss) at D14 relative to baseline, as well as the functional recovery of hearing from 24 h to D14 (ABR threshold shift & DPOAE amplitude loss) were determined for all treatment groups.

Figure 4:
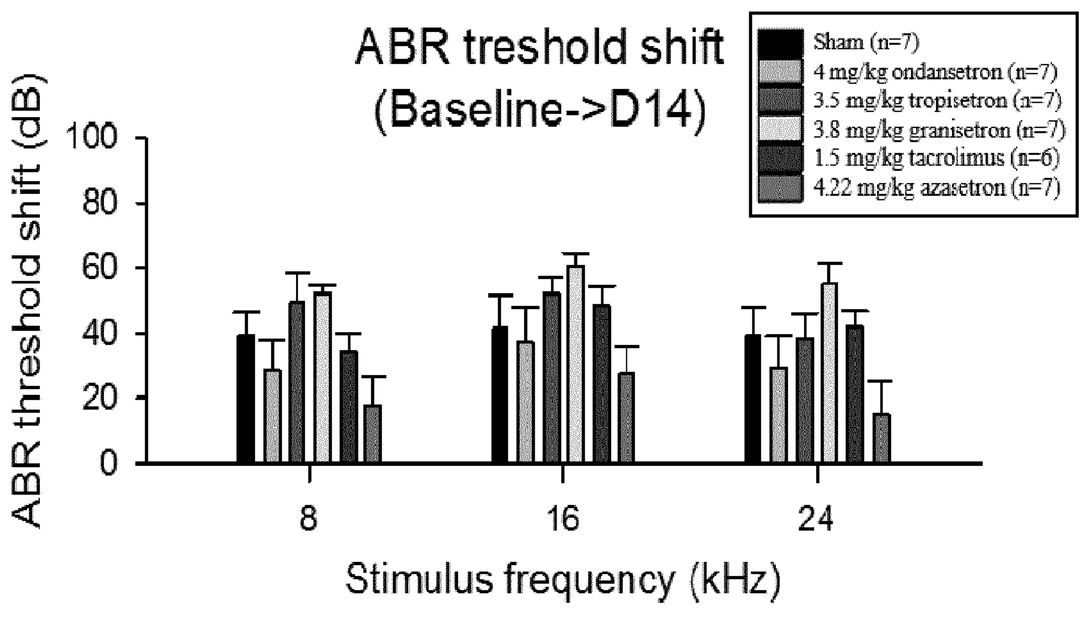
FIG. 4 is a histogram showing the ABR threshold shift from baseline to D14 for all treatment groups.
Figure 5:
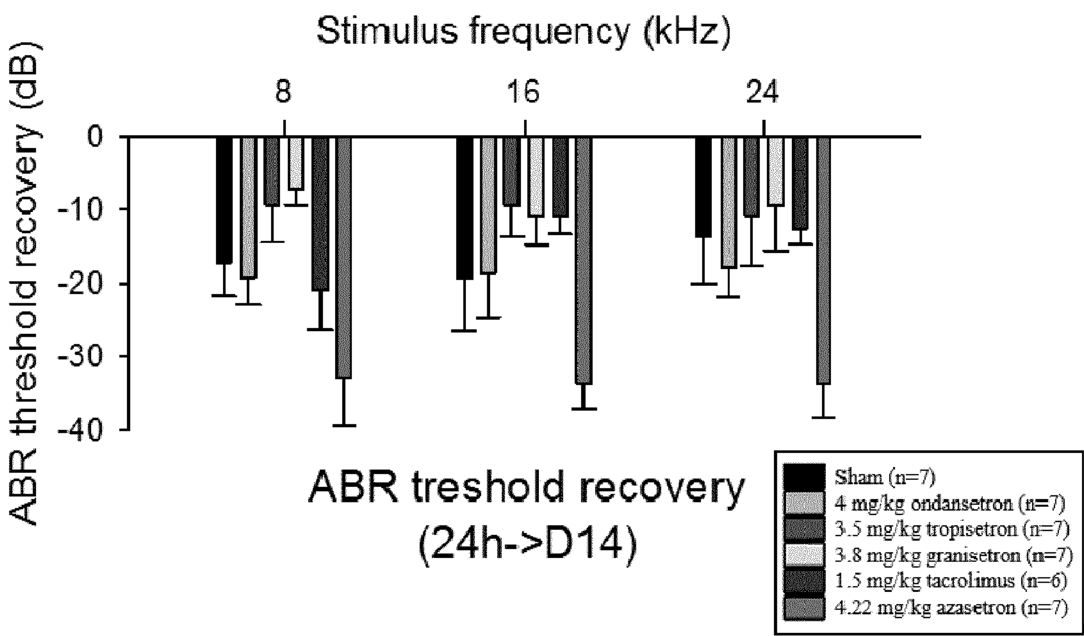
FIG. 5 is a histogram showing the ABR threshold recovery from 24 h after acoustic trauma to D14 for all treatment groups.

The azasetron HCl treated group had both significantly lower ABR threshold shifts at day 14 (FIG. 4, $p=0.003$) and better ABR threshold recovery from 24 h to day 14 (FIG. 5, $p<0.001$) compared to placebo, while the ondansetron HCl treated group had a lower ABR threshold shift at day 14 (FIG. 4) compared to placebo (not reaching significance). The granisetron HCl and tropisetron HCl treated groups showed strong trends towards higher ABR threshold shifts (FIG. 4) and decreased threshold recovery. Treatment with the specific calcineurin inhibitor tacrolimus had no major effect on ABR threshold measures.

Figure 6:
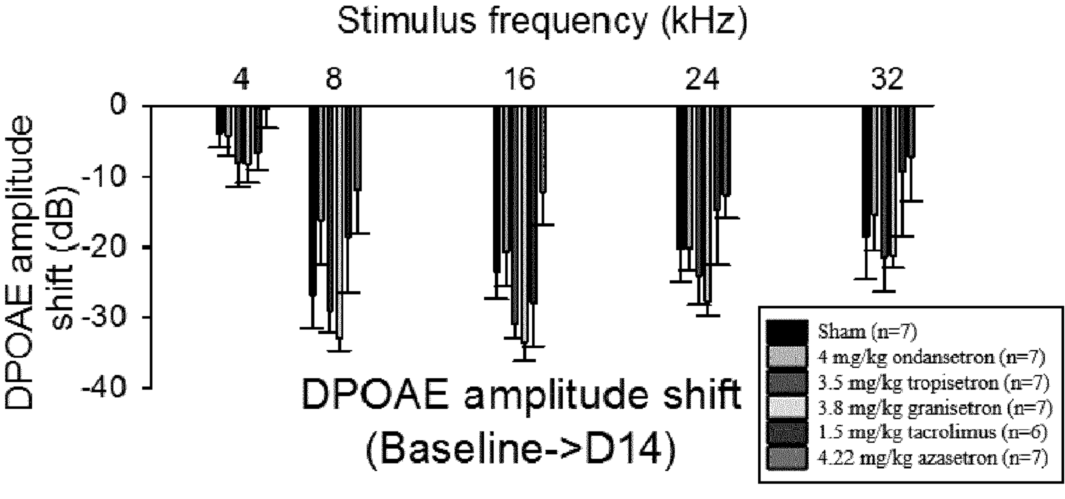
FIG. 6 is a histogram showing DPOAE amplitude loss from baseline to D14 for all treatment groups.
Figure 7:
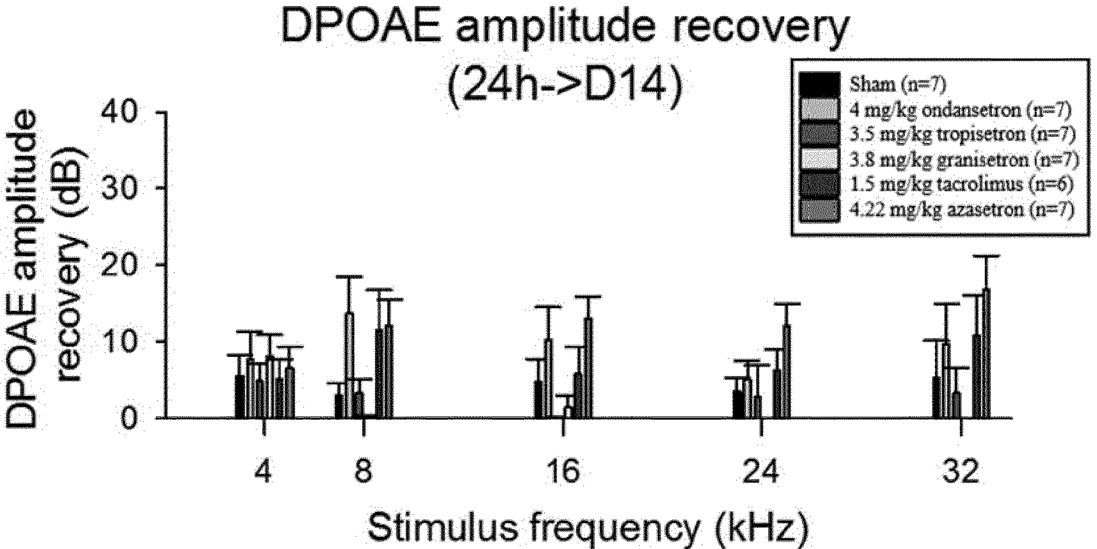
FIG. 7 is a histogram showing DPOAE amplitude recovery from 24 h after acoustic trauma to D14 for all treatment groups.

Compared to the placebo treated group, azasetron HCl treatment resulted in significantly reduced loss of DPOAE amplitudes ($p<0.001$) from baseline to day 14 (FIG. 6) as well as significantly improved recovery of DPOAE amplitudes ($p<0.001$) from 24 h post trauma to day 14 (FIG. 7), suggesting reduced loss of outer hair cells in the cochlea. While there was trend towards reduced loss of DPOAE amplitude and improved recovery in the ondansetron HCl and tacrolimus treated groups at some frequencies, this did not reach statistical significance. Neither did the trend towards increased DPOAE amplitude loss and reduced recovery after granisetron HCl or tropisetron HCl treatment.

To further support the conclusions from the functional audiometry data, the loss of outer hair cells in four treatment group was determined by constructing cytocochleograms from histological preparations of cochleae fixed after audiometry on day 14.

Figure 8:
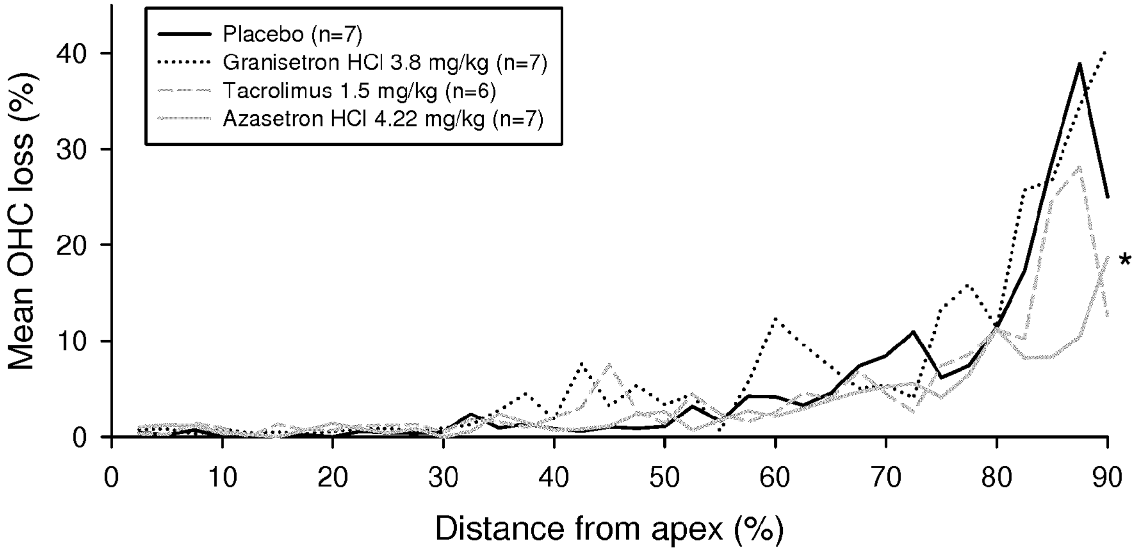
FIG. 8 is a graph showing mean outer hair cell loss as a function normalized distance from apex for groups treated with placebo, granisetron, tacrolimus or azasetron in cochleae fixed at D14 after acoustic trauma.

Consistent with the significantly reduced loss of DPOAE amplitudes after azasetron HCl treatment, this group also displayed significantly lower mean loss (FIG. 8) of outer hair cells (OHC, the source of the DPOAE signals) compared to placebo ($p<0.05$). Neither the granisetron HCl nor the tacrolimus treated groups were significantly different from placebo.

Altogether, the data demonstrate a significant and strong treatment effect of the calcineurin inhibiting setron family member azasetron, and similar trends for ondansetron, on functional and histological measures of noise-induced hearing loss.

Indeed, compared to placebo treatment, ABR thresholds shifts induced by azasetron treatment were reduced by ~35-60% (for ondansetron treatment, ~10-30%), DPOAE amplitudes loss by ~60% (for ondansetron ~10-30%) and mean outer hair cell loss by ~50-75%.

Conversely, granisetron (a setron compound with no calcineurin inhibiting effect) and tropisetron had a negative impacts on ABR threshold shifts (~17-40% higher threshold shift at day 14 than placebo) a trend towards worse DPOAE amplitudes and OHC loss.

Treatment with the specific calcineurin inhibitor tacrolimus showed trends towards improving DPOAE amplitude loss at some frequencies, but had no effect on ABR threshold shifts in this realistic hearing loss (initial severe threshold shifts of up to 70 dB) and treatment (treatments only initiated after acoustic overexposure) paradigm. This in contrast to previously published results with specific calcineurin inhibitors using either a milder hearing loss paradigm (~10 dB initial ABR threshold shifts), treatment initiation prior to acoustic trauma or both (Uemaetomari et al. 2005, Hearing Res 209:86-90; Bas et al. 2009, Acta Oto-Laryngologica 129:385-389).

In conclusion, these data demonstrate significant protective effects of treatment with the calcineurin inhibiting setron family member azasetron with similar trends for ondansetron in model of severe sensorineural hearing loss (even outperforming the specific calcineurin inhibitor tacrolimus), while the setron family member granisetron lacking the capacity to inhibit calcineurin had no or even deleterious effects on hearing outcomes. These data supports the use of calcineurin inhibiting setron family members, in particular azasetron and ondansetron, in the treatment of sensorineural hearing loss. The significant ABR threshold improvements determined for the azasetron treated group corresponds to "marked improvement to complete recovery" compared to only "slight improvement" for the placebo group, according to typical clinical audiological criteria (Furuhashi et al. 2002, Clin Otolaryngol 27:458-463). Similarly, recent clinical research data has demonstrated that the early preservation or improvement of DPOAE responses (a significant effect of azasetron treatment) is highly predictive for significant long term improvement of hearing capability in patients suffering idiopathic sudden sensorineural hearing loss (Shupak et al. 2014, Otol Neurotol 35(10):1691-1697).

The invention claimed is:

1. A method for preventing hearing loss in a subject in need thereof, comprising administering to said subject an inhibitor of calcineurin of the setron family selected from azasetron, ondansetron and pharmaceutically acceptable salts thereof, wherein administration of the inhibitor of calcineurin of the setron family is started prior to the onset of the hearing loss to be prevented.

2. The method according to claim 1, wherein the inhibitor of calcineurin of the setron family is azasetron or a pharmaceutically acceptable salt thereof.

3. The method according to claim 1, wherein said hearing loss is sensorineural hearing loss.

4. The method according to claim 3, wherein said sensorineural hearing loss is noise-induced sensorineural hearing loss, age-related sensorineural hearing loss, ototoxic drug-induced sensorineural hearing loss, or idiopathic sensorineural hearing loss.

5. The method according to claim 3, wherein said sensorineural hearing loss is noise-induced sensorineural hearing loss or age-related sensorineural hearing loss.

6. The method according to claim 3, wherein said sensorineural hearing loss is ototoxic drug-induced sensorineural hearing loss.

7. The method according to claim 6, wherein the ototoxic drug inducing sensorineural hearing loss is selected from the group consisting of aminoglycosides, chemotherapeutic agents, loop diuretics, antimetabolites and salicylates.

8. The method according to claim 1, wherein said hearing loss is a decrease in hearing of at least about 20 dB over at least three contiguous frequencies.

9. The method according to claim 1, wherein said hearing loss is total deafness.

10. The method according to claim 1, wherein said hearing loss is unilateral or bilateral.

11. The method according to claim 1, wherein said hearing loss is sudden sensorineural hearing loss.

12. The method according to claim 1, wherein the inhibitor of calcineurin of the setron family is systemically administered, topically administered, or intra-tympanically injected.

13. The method according to claim 1, wherein the inhibitor of calcineurin of the setron family is administered 1 to 3 times a day.

14. The method according to claim 1, wherein the inhibitor of calcineurin of the setron family is administered for at least 30 days.

15. The method according to claim 4, wherein administration of the inhibitor of calcineurin of the setron family is started prior to the exposure to a noise or agent that may cause sensorineural hearing loss.

16. The method according to claim 4, wherein said sensorineural hearing loss is noise-induced sensorineural hearing loss and wherein administration of the inhibitor of calcineurin of the setron family is started prior to the exposure to a noise that may cause the noise-induced sensorineural hearing loss.

17. The method according to claim 4, wherein said sensorineural hearing loss is ototoxic drug-induced sensorineural hearing loss and wherein administration of the inhibitor of calcineurin of the setron family is started prior to the exposure to an agent that may cause the ototoxic drug-induced sensorineural hearing loss.

* * * * *